United States Patent
Fukuda et al.

(10) Patent No.: US 12,312,581 B2
(45) Date of Patent: May 27, 2025

(54) CELL-CONTAINING HYDROGEL BODY AND METHOD FOR PRODUCING SAME

(71) Applicants: National University Corporation Yokohama National University, Kanagawa (JP); Kanagawa Institute of Industrial Science and Technology, Kanagawa (JP)

(72) Inventors: Junji Fukuda, Yokohama (JP); Tatsuto Kageyama, Yokohama (JP)

(73) Assignees: National University Corporation YOKOHAMA National University, Yokohama (JP); Kanagawa Institute of Industrial Science and Technology, Ebina (JP)

( * ) Notice: Subject to any disclaimer, the term of this patent is extended or adjusted under 35 U.S.C. 154(b) by 1181 days.

(21) Appl. No.: 17/047,761

(22) PCT Filed: Apr. 16, 2019

(86) PCT No.: PCT/JP2019/016332
§ 371 (c)(1),
(2) Date: Oct. 15, 2020

(87) PCT Pub. No.: WO2019/220843
PCT Pub. Date: Nov. 21, 2019

(65) Prior Publication Data
US 2021/0163918 A1    Jun. 3, 2021

(30) Foreign Application Priority Data
May 16, 2018 (JP) ................. 2018-094499

(51) Int. Cl.
| | |
|---|---|
| *A61L 27/14* | (2006.01) |
| *A61L 27/24* | (2006.01) |
| *A61L 27/38* | (2006.01) |
| *A61L 27/52* | (2006.01) |
| *C12N 5/00* | (2006.01) |
| *C12N 5/071* | (2010.01) |
| *C12N 5/077* | (2010.01) |
| *C12N 11/04* | (2006.01) |
| *C12N 11/098* | (2020.01) |

(52) U.S. Cl.
CPC ........... *C12N 11/098* (2020.01); *A61L 27/24* (2013.01); *A61L 27/3813* (2013.01); *A61L 27/3834* (2013.01); *A61L 27/3886* (2013.01); *A61L 27/52* (2013.01); *C12N 5/0625* (2013.01); *C12N 5/0652* (2013.01); *C12N 11/04* (2013.01)

(58) Field of Classification Search
CPC .. A61L 27/14; A61L 27/3813; A61L 27/3834; A61L 27/3886; A61L 27/52; C12N 5/06; C12N 11/04
See application file for complete search history.

(56) References Cited

U.S. PATENT DOCUMENTS

| | | | | |
|---|---|---|---|---|
| 5,712,161 | A | * 1/1998 | Koezuka et al. | ........ C12N 5/00 435/382 |
| 2008/0220524 | A1 | * 9/2008 | Noll et al. | ............... C12M 3/00 435/395 |
| 2009/0280469 | A1 | 11/2009 | Jujiwara et al. | |
| 2010/0021866 | A1 | 1/2010 | Tsuji et al. | |
| 2013/0109093 | A1 | 5/2013 | Tsuji et al. | |
| 2014/0037592 | A1 | 2/2014 | Toyoshima et al. | |
| 2014/0106432 | A1 | 4/2014 | Fujiwara et al. | |
| 2016/0160185 | A1 | 6/2016 | Fujiwara et al. | |
| 2016/0184481 | A1 | 6/2016 | Thangapazham et al. | |
| 2019/0062687 | A1 | 2/2019 | Fukuda et al. | |
| 2019/0328790 | A1 | 10/2019 | Fukuda et al. | |

FOREIGN PATENT DOCUMENTS

| | | |
|---|---|---|
| EP | 1905459 A1 | 4/2008 |
| EP | 2674484 A1 | 12/2013 |
| JP | 2003-070466 A | 3/2003 |

(Continued)

OTHER PUBLICATIONS

Napolitano et al. (2007) "Dynamics of the self-assembly of complex cellular aggregates on micromolded nonadhesive hydrogels" Tissue engineering, 13(8), 2087-2094. (Year: 2007).*
Nakao et al. (2007) "The development of a bioengineered organ germ method" Nature methods, 4(3), 227-230. (Year: 2007).*
Machine translation of WO 2017/217393 A1 generated by Espacenet. com (European Patent Office). (Year: 2024).*
Nanmo et al. (2023) "Bioprinting of hair follicle germs for hair regenerative medicine" Acta biomaterialia, 165, 50-59. (Year: 2023).*
International Search Report (ISR) issued in corresponding International Patent Application No. PCT/JP2019/016332 dated Jul. 16, 2019.
Extended European Search Report issued in corresponding European Patent Application No. 19803757.4 dated Mar. 4, 2022.

(Continued)

*Primary Examiner* — Laura Schuberg
*Assistant Examiner* — James Joseph Graber
(74) *Attorney, Agent, or Firm* — Morgan, Lewis & Bockius LLP

(57) ABSTRACT

Provided are a cell-containing hydrogel body and a method of producing the same, which enable simple and effective control of the size of a boundary surface for an interaction between cells. The method of producing a cell-containing hydrogel body includes: forming, under a gas phase, a first hydrogel droplet on a surface of a substrate, the first hydrogel droplet containing first cells being dispersed therein and a first hydrogel polymer; forming, under a gas phase, a second hydrogel droplet on the surface, the second hydrogel droplet containing second cells being dispersed therein and a second hydrogel polymer, the second hydrogel droplet being combined with the first hydrogel droplet; and forming, under a gas phase, a cell-containing hydrogel body on the surface by gelling a hydrogel droplet-combined body including a first droplet portion derived from the first hydrogel droplet and a second droplet portion derived from the second hydrogel droplet.

19 Claims, 10 Drawing Sheets

(56) References Cited

FOREIGN PATENT DOCUMENTS

| JP | 2008-029331 A | 2/2008 | |
|---|---|---|---|
| JP | 2016-522682 A | 8/2016 | |
| JP | 2017-051160 A | 3/2017 | |
| JP | WO2017217393 A1 * | 12/2017 | ............. C12N 5/077 |
| WO | 2006/129672 A1 | 12/2006 | |
| WO | 2012/108069 A1 | 8/2012 | |
| WO | 2014/030722 A1 | 2/2014 | |
| WO | 2017/073625 A1 | 5/2017 | |
| WO | 2017/217393 A1 | 12/2017 | |

OTHER PUBLICATIONS

Kageyama et al., "Spontaneous hair follicle germ (HFG) formation in vitro, enabling the large-scale production of HFGs for regenerative medicine," Biomaterials, 154: 291-300 (2018).

* cited by examiner

CELL-CONTAINING HYDROGEL BODY AND METHOD FOR PRODUCING SAME

TECHNICAL FIELD

The present invention relates to a cell-containing hydrogel body and a method of producing the same.

BACKGROUND ART

In Patent Literature 1, there is a description that regenerated hair follicle primordia were prepared by adding a cell mixture suspension of epithelial cells and mesenchymal cells collected from a mouse embryo to a microwell plate having regularly arranged microwell portions, and culturing a mixture of the cells while supplying oxygen thereto.

In Patent Literature 2, there is a description of a method of producing a cell mass, involving adding a Wnt signal activator to a mixed cell culture solution, which contains hair papilla cells and keratinocytes, and culturing the culture solution containing the Wnt signal activator by a hanging drop method.

In Patent Literature 3, there is a description of a method involving forming a cell lump of hair follicle mesenchymal cells in a culture solution, and then allowing the cell lump to coexist with epithelial cells in the culture solution to cause the epithelial cells to undergo cell adhesion to the periphery of the cell lump of the hair follicle mesenchymal cells through a cell sorting phenomenon, to thereby produce an artificial hair bulb in which the epithelial cells are in cell adhesion to the outside of the cell lump of the hair follicle mesenchymal cells. In Patent Literature 3, there is also a description of a method involving allowing hair follicle mesenchymal cells and epithelial cells to coexist in a culture solution to form a cell lump of the hair follicle mesenchymal cells, and cause the epithelial cells to undergo cell adhesion to the periphery of the cell lump, through a cell sorting phenomenon, to thereby produce an artificial hair bulb in which the epithelial cells are in cell adhesion to the outside of the cell lump of the hair follicle mesenchymal cells.

CITATION LIST

Patent Literature

[PTL 1] WO 2017/073625 A1
[PTL 2] JP 2008-029331 A
[PTL 3] JP 2003-070466 A

SUMMARY OF INVENTION

Technical Problem

However, hitherto, in the case of using two or more kinds of cells, it has not been easy to control the size of a boundary surface at which the cells of one kind interact with the cells of another kind.

The present invention has been made in view of the above-mentioned problem, and one of the objects of the present invention is to provide a cell-containing hydrogel body and a method of producing the same, which enable simple and effective control of the size of a boundary surface for an interaction between cells.

Solution to Problem

In order to achieve the above-mentioned object, according to one embodiment of the present invention, there is provided a method of producing a cell-containing hydrogel body, including: forming, under a gas phase, a first hydrogel droplet on a surface of a substrate, the first hydrogel droplet containing first cells being dispersed therein and a first hydrogel polymer; forming, under a gas phase, a second hydrogel droplet on the surface, the second hydrogel droplet containing second cells being dispersed therein and a second hydrogel polymer, the second hydrogel droplet being combined with the first hydrogel droplet; and forming, under a gas phase, a cell-containing hydrogel body on the surface by gelling a hydrogel droplet-combined body including a first droplet portion derived from the first hydrogel droplet and a second droplet portion derived from the second hydrogel droplet. According to the one embodiment of the present invention, a method of producing a cell-containing hydrogel body, which enables simple and effective control of the size of a boundary surface for an interaction between cells, is provided.

The method may further include culturing the first cells and the second cells in the cell-containing hydrogel body. In this case, the first cells and the second cells in the cell-containing hydrogel body may be cultured after the cell-containing hydrogel body is removed from the surface. Further, in this case, the first cells and the second cells may be cultured in the cell-containing hydrogel body in a floating state after the cell-containing hydrogel body is removed from the surface.

In addition, in the method, the first cells and the second cells in the cell-containing hydrogel body may be cultured to provide a cell-containing hydrogel body containing a first cell aggregate formed through aggregation of the first cells and/or a second cell aggregate formed through aggregation of the second cells.

In addition, in the method, the first cells and the second cells in the cell-containing hydrogel body may be cultured to provide a cell-containing hydrogel body having the following property (a) and/or property (b): (a) the cell-containing hydrogel body contains the first cell aggregate and a first hydrogel covering portion covering the first cell aggregate, and a density of the first hydrogel polymer inside the first cell aggregate is higher than that in the first hydrogel covering portion; (b) the cell-containing hydrogel body contains the second cell aggregate and a second hydrogel covering portion covering the second cell aggregate, and a density of the second hydrogel polymer inside the second cell aggregate is higher than that in the second hydrogel covering portion.

In addition, in the method, the first hydrogel polymer may have a cell binding property with respect to the first cells, and/or the second hydrogel polymer may have a cell binding property with respect to the second cells. In addition, in the method, a combination of the first cells and the second cells may be a combination of epithelial cells and mesenchymal cells.

In order to achieve the above-mentioned object, according to one embodiment of the present invention, there is provided a cell-containing hydrogel body, including: a first hydrogel portion, which is a gelled body of a first hydrogel droplet containing first cells and a first hydrogel polymer; and a second hydrogel portion, which is a gelled body of a second hydrogel droplet containing second cells and a second hydrogel polymer, and which is combined with the first hydrogel portion, wherein the first hydrogel portion contains a first cell aggregate that is an aggregated body of the first cells, and/or wherein the second hydrogel portion contains a second cell aggregate that is an aggregated body of the second cells. According to the one embodiment of the present invention, a cell-containing hydrogel body, in which the size of a boundary surface for an interaction between cells is simply and effectively controlled, is provided.

The cell-containing hydrogel body may have the following property (a) and/or property (b): (a) the cell-containing hydrogel body contains the first cell aggregate and a first hydrogel covering portion covering the first cell aggregate, and a density of the first hydrogel polymer inside the first cell aggregate is higher than that in the first hydrogel covering portion; (b) the cell-containing hydrogel body contains the second cell aggregate and a second hydrogel covering portion covering the second cell aggregate, and a density of the second hydrogel polymer inside the second cell aggregate is higher than that in the second hydrogel covering portion.

In addition, in the cell-containing hydrogel body, the first hydrogel polymer may have a cell binding property with respect to the first cells, and/or the second hydrogel polymer may have a cell binding property with respect to the second cells. In addition, in the cell-containing hydrogel body, a combination of the first cells and the second cells may be a combination of epithelial cells and mesenchymal cells. In addition, the cell-containing hydrogel body may be in a floating state in a solution.

Advantageous Effects of Invention

According to the present invention, a cell-containing hydrogel body and a method of producing the same, which enable simple and effective control of the size of a boundary surface for an interaction between cells, are provided.

DESCRIPTION OF EMBODIMENTS

Figure 1A:
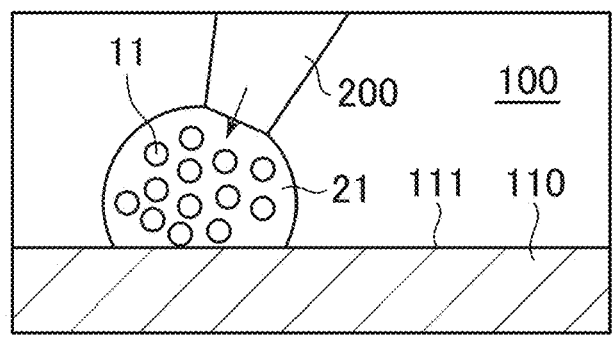
FIG. 1A is an explanatory diagram for schematically illustrating some operations included in an example of a method of producing a cell-containing hydrogel body according to one embodiment of the present invention.

Now, embodiments of the present invention will be described. The present invention is not limited to these embodiments.

In FIG. 1A to FIG. 1E, operations included in an example of a method of producing a cell-containing hydrogel body according to one embodiment of the present invention (hereinafter referred to as "method of the present invention") are schematically illustrated. The method of the present invention includes: forming, under a gas phase 100, a first hydrogel droplet 21 on a surface 111 of a substrate 110, the first hydrogel droplet 21 containing first cells 11 being dispersed therein and a first hydrogel polymer; forming, under the gas phase 100, a second hydrogel droplet 22 on the surface 111, the second hydrogel droplet 22 containing second cells 12 being dispersed therein and a second hydrogel polymer, the second hydrogel droplet 22 being combined with the first hydrogel droplet 21; and forming, under the gas phase 100, a cell-containing hydrogel body 40 on the surface 111 by gelling a hydrogel droplet-combined body 30 including a first droplet portion 31 derived from the first hydrogel droplet 21 and a second droplet portion 32 derived from the second hydrogel droplet 22.

Figure 1B:
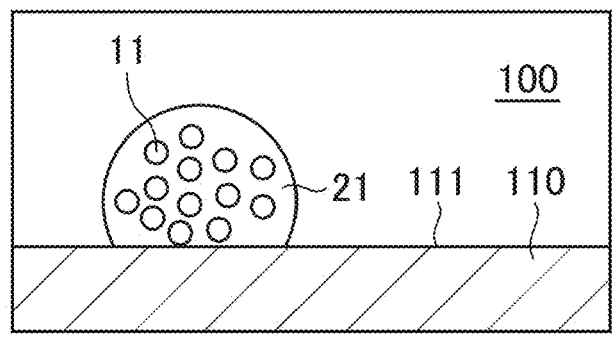
FIG. 1B is an explanatory diagram for schematically illustrating other operations included in an example of the method of producing a cell-containing hydrogel body according to one embodiment of the present invention.

That is, in the method of the present invention, first, as illustrated in FIG. 1A and FIG. 1B, the first hydrogel droplet 21 is formed on the surface 111 of the substrate 110 in the gas phase 100. The first hydrogel droplet 21 contains the dispersed first cells 11 and the first hydrogel polymer.

The first hydrogel droplet 21 is formed by dropping a first hydrogel aqueous solution containing the dispersed first cells 11 and the first hydrogel polymer onto the surface 111 of the substrate 110. In the example illustrated in FIG. 1A, the first hydrogel droplet 21 is formed by dropping the first hydrogel aqueous solution onto the surface 111 of the substrate 110 through use of a pipette 200.

The volume of the first hydrogel droplet 21 is not particularly limited, but may be, for example, 0.01 μL or more and 1 mL or less, 0.1 μL or more and 100 μL or less, or 1 μL or more and 10 μL or less.

The density of the first cells 11 contained in the first hydrogel droplet 21 is not particularly limited, but may be, for example, $1\times10^2$ cells/mL or more and $1\times10^9$ cells/mL or less, $1\times10^3$ cells/mL or more and $1\times10^8$ cells/mL or less, $1\times10^4$ cells/mL or more and $1\times10^8$ cells/mL or less, $1\times10^5$ cells/mL or more and $1\times10^7$ cells/mL or less, or $1\times10^6$ cells/mL or more and $1\times10^7$ cells/mL or less.

The first hydrogel droplet 21 mainly contains the first cells 11 as cells. That is, the ratio of the number of the first cells 11 to the total number of cells contained in the first hydrogel droplet 21 may be, for example, 50% or more, and is preferably 60% or more, more preferably 70% or more, still more preferably 80% or more, and particularly preferably 90% or more.

Figure 1C:
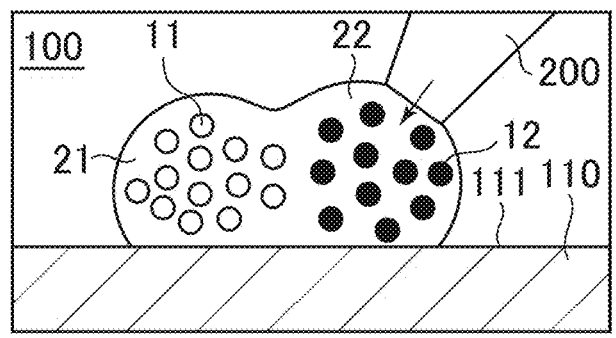
FIG. 1C is an explanatory diagram for schematically illustrating still other operations included in an example of the method of producing a cell-containing hydrogel body according to one embodiment of the present invention.

In the method of the present invention, after the first hydrogel droplet 21 is formed on the surface 111 of the substrate 110, as illustrated in FIG. 1C, the second hydrogel droplet 22 combined with the first hydrogel droplet 21 is formed on the surface 111 in the gas phase 100. The second hydrogel droplet 22 contains the dispersed second cells 12 and the second hydrogel polymer.

The second hydrogel droplet 22 is formed by dropping a second hydrogel aqueous solution containing the dispersed second cells 12 and the second hydrogel polymer to a position on the surface 111 of the substrate 110 so that the second hydrogel droplet 22 becomes adjacent to the first hydrogel droplet 21 and the second hydrogel droplet 22 comes into contact with the first hydrogel droplet 21. As a result, a part of the second hydrogel droplet 22 is brought into contact with the surface 111, and another part thereof is brought into contact with the first hydrogel droplet 21. In the example illustrated in FIG. 1C, the second hydrogel droplet 22 is formed by dropping the second hydrogel aqueous solution onto the surface 111 of the substrate 110 through use of the pipette 200.

The volume of the second hydrogel droplet 22 is not particularly limited, but may be, for example, 0.01 μL or more and 1 mL or less, 0.1 μL or more and 100 μL or less, or 1 μL or more and 10 μL or less.

The density of the second cells 12 contained in the second hydrogel droplet 22 is not particularly limited, but may be, for example, $1\times10^2$ cells/mL or more and $1\times10^9$ cells/mL or less, $1\times10^3$ cells/mL or more and $1\times10^8$ cells/mL or less, $1\times10^4$ cells/mL or more and $1\times10^8$ cells/mL or less, $1\times10^5$ cells/mL or more and $1\times10^7$ cells/mL or less, or $1\times10^6$ cells/mL or more and $1\times10^7$ cells/mL or less.

The second hydrogel droplet 22 mainly contains the second cells 12 as cells. That is, the ratio of the number of the second cells 12 to the total number of cells contained in the second hydrogel droplet 22 may be, for example, 50% or more, 60% or more, 70% or more, 80% or more, or 90% or more.

Figure 1D:
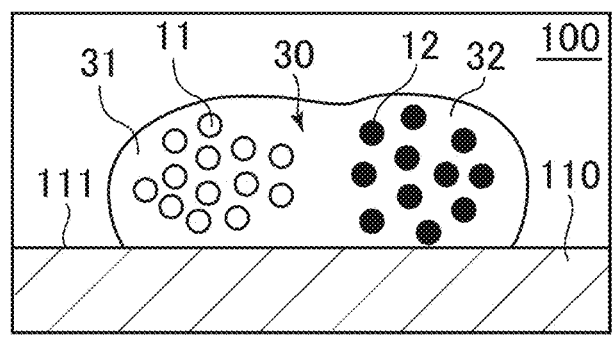
FIG. 1D is an explanatory diagram for schematically illustrating still other operations included in an example of the method of producing a cell-containing hydrogel body according to one embodiment of the present invention.

Then, in the method of the present invention, as illustrated in FIG. 1D, the hydrogel droplet-combined body 30 (hereinafter referred to simply as "droplet-combined body 30") including the first droplet portion 31 derived from the first hydrogel droplet 21 and the second droplet portion 32 derived from the second hydrogel droplet 22 is formed on the surface 111 in the gas phase 100.

The first droplet portion 31 of the droplet-combined body 30 contains the dispersed first cells 11 and the first hydrogel polymer. In addition, the second droplet portion 32 of the droplet-combined body 30 contains the dispersed second cells 12 and the second hydrogel polymer. In the droplet-combined body 30, the first droplet portion 31 and the second droplet portion 32 each have a part thereof brought into contact with the surface 111, and are combined with each other at other parts thereof.

The first hydrogel droplet 21 and the second hydrogel droplet 22 contain the first hydrogel polymer and the second hydrogel polymer, respectively, and hence each have higher viscosity and specific gravity than water. Accordingly, although the droplet-combined body 30 formed on the surface 111 in the gas phase 100 is a liquid and hence has fluidity, as illustrated in FIG. 1D, the first cells 11 and the second cells 12 are maintained in the state of being dispersed in the first droplet portion 31 and the second droplet portion 32 of the droplet-combined body 30, respectively.

The dispersed cells are cells that are dispersed and floating in a solution, each of which is not bound to other cells or only bound to several cells. For example, when a cell suspension containing dispersed cells is centrifuged in order to separate the cells and a solvent contained in the cell suspension, a pellet of the cells formed after the centrifugation is an aggregate of the cells, and the cells constituting the pellet are not dispersed cells.

In the example illustrated in FIG. 1A to FIG. 1E, the droplet-combined body 30 is formed of the two hydrogel droplet portions 31 and 32, but may be formed by, for example, similarly combining three or more hydrogel droplets.

That is, for example, after the droplet-combined body 30 formed of the first hydrogel droplet portion 31 and the second hydrogel droplet portion 32 is formed on the surface 111, a third hydrogel droplet containing dispersed third cells and a third hydrogel polymer may be further formed on the surface 111 in the gas phase 100 so as to be combined with the droplet-combined body 30, to thereby form a droplet-combined body 30 that further contains a third hydrogel droplet portion derived from the third hydrogel droplet.

The volume of the droplet-combined body 30 which is finally formed on the surface 111 is not particularly limited, but may be, for example, 0.02 µL or more and 100 mL or less, 0.2 µL or more and 10 mL or less, or 2 µL or more and 1 mL or less.

The density of the cells contained in the droplet-combined body 30 is not particularly limited, but may be, for example, $1 \times 10^2$ cells/mL or more and $1 \times 10^9$ cells/mL or less, $1 \times 10^3$ cells/mL or more and $1 \times 10^8$ cells/mL or less, $1 \times 10^4$ cells/mL or more and $1 \times 10^8$ cells/mL or less, $1 \times 10^5$ cells/mL or more and $1 \times 10^7$ cells/mL or less, or $1 \times 10^6$ cells/mL or more and $1 \times 10^7$ cells/mL or less.

Figure 2:
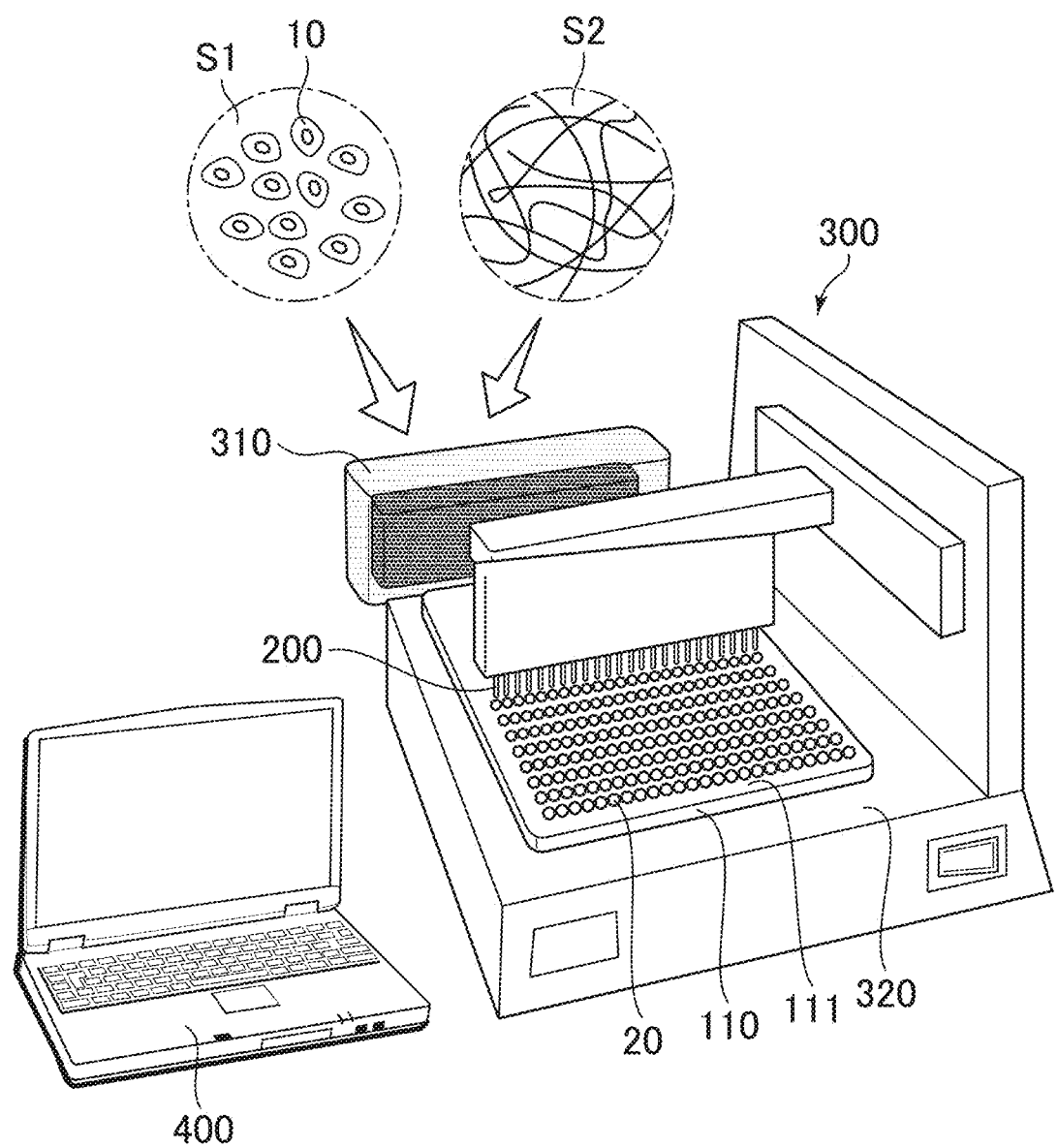
FIG. 2 is an explanatory diagram for schematically illustrating an automatic dispensing system to be used in an example of the method of producing a cell-containing hydrogel body according to one embodiment of the present invention.

For such dropping of the hydrogel droplets 21 and 22 as described above, for example, as illustrated in FIG. 2, an automatic dispensing system 300 including a plurality of the pipettes 200 that are regularly arranged is preferably used. The automatic dispensing system 300 illustrated in FIG. 2 includes a tank 310 configured to accommodate a mixed aqueous solution of an aqueous solution S1 containing dispersed cells 10 and a hydrogel aqueous solution S2 containing a hydrogel polymer, and a stage 320 on which the substrate 110 is to be placed, with operation of the dispensing system being controlled by a computer 400.

Through use of the automatic dispensing system 300, a plurality of regularly arranged hydrogel droplets 20 are efficiently formed on the surface 111 of the substrate 110 by dropping the mixed aqueous solution in the tank 310 from each of the plurality of the pipettes 200 onto the surface 111.

Figure 3A:
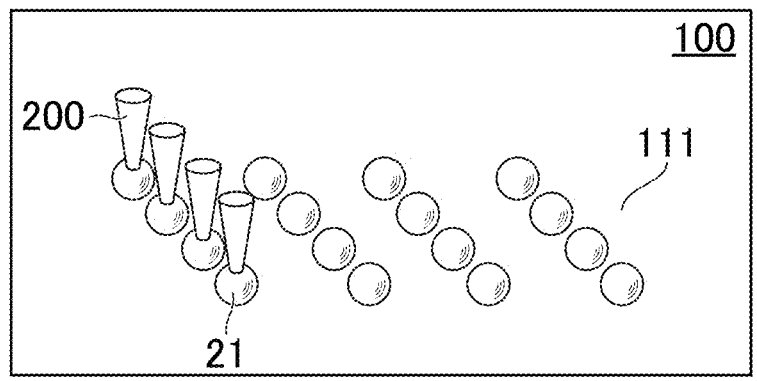
FIG. 3A is an explanatory diagram for schematically illustrating some operations, which involve using the automatic dispensing system, included in an example of the method of producing a cell-containing hydrogel body according to one embodiment of the present invention.
Figure 3B:
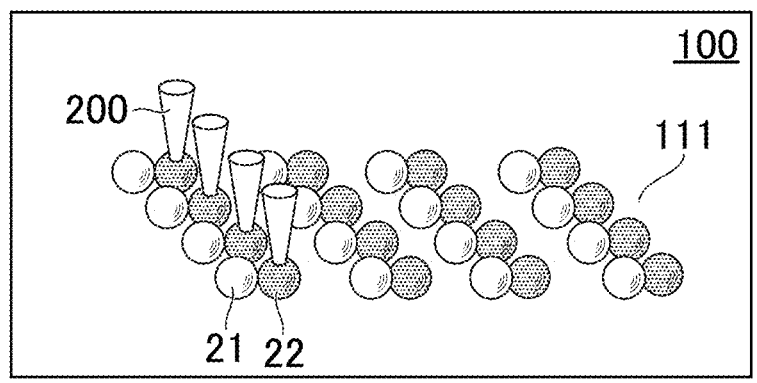
FIG. 3B is an explanatory diagram for schematically illustrating other operations, which involve using the automatic dispensing system, included in an example of the method of producing a cell-containing hydrogel body according to one embodiment of the present invention.
Figure 3C:
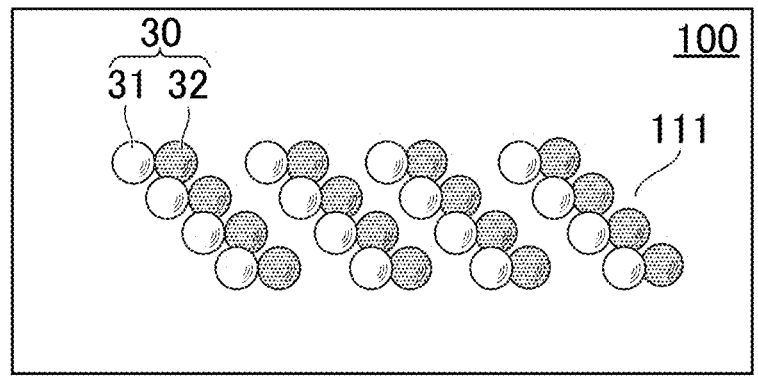
FIG. 3C is an explanatory diagram for schematically illustrating still other operations, which involve using the automatic dispensing system, included in an example of the method of producing a cell-containing hydrogel body according to one embodiment of the present invention.

In FIG. 3A to FIG. 3C, examples of operations involving using the automatic dispensing system 300 are schematically illustrated. First, as illustrated in FIG. 3A, a plurality of the first hydrogel droplets 21 are dropped from the plurality of the pipettes 200 onto the surface 111 in the gas phase 100. Then, as illustrated in FIG. 3B, a plurality of the second hydrogel droplets 22 are dropped from the plurality of the pipettes 200 onto the surface 111 so as to each be combined with one of the plurality of the first hydrogel droplets 21. As a result, as illustrated in FIG. 3C, a plurality of the droplet-combined bodies 30 are formed, regularly arranged on the surface 111 and each formed of the first droplet portion 31 and the second droplet portion 32.

Figure 4:
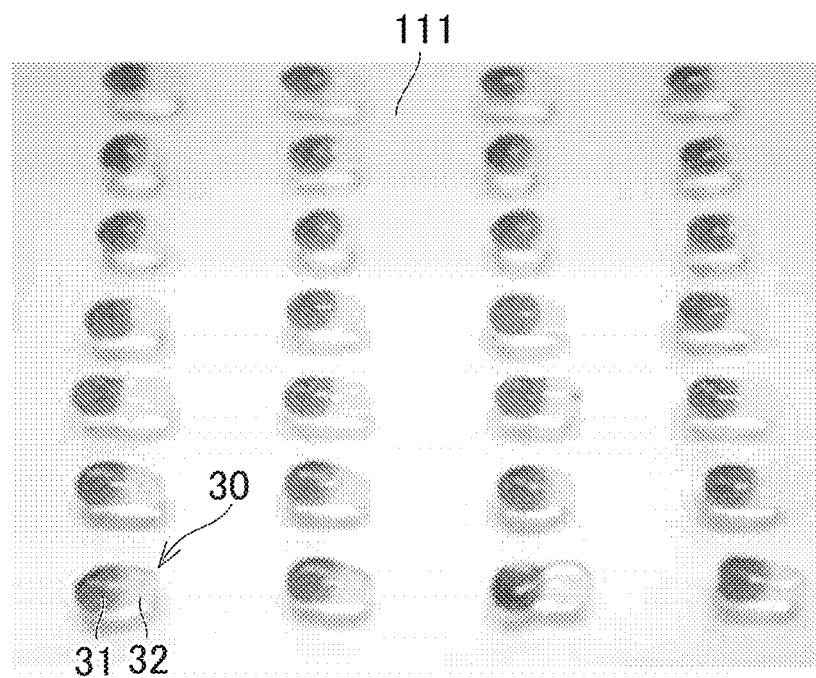
FIG. 4 is an explanatory diagram showing a photograph of hydrogel droplet-combined bodies formed using an automatic dispensing apparatus in an example of the method of producing a cell-containing hydrogel body according to one embodiment of the present invention.

In FIG. 4, a photograph of the droplet-combined bodies 30 actually formed using the automatic dispensing system 300 is shown. In each of the plurality of the droplet-combined bodies 30 regularly arranged on the surface 111 shown in FIG. 4, a colored left half is the first hydrogel droplet portion 31 having a dye added thereto in order to enhance visibility, and an uncolored right half is the second hydrogel droplet portion 32.

Figure 1E:
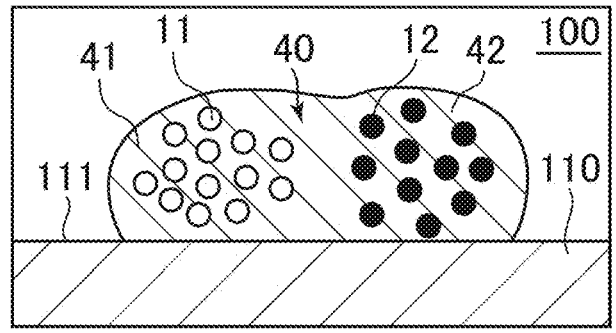
FIG. 1E is an explanatory diagram for schematically illustrating still other operations included in an example of the method of producing a cell-containing hydrogel body according to one embodiment of the present invention.

In the method of the present invention, as illustrated in FIG. 1E, the cell-containing hydrogel body 40 (hereinafter referred to simply as "hydrogel body 40") is formed on the surface 111 in the gas phase 100 by further gelling the droplet-combined body 30.

Through the gelling, the hydrogel polymers contained in the droplet-combined body 30 form an intermolecular network, and the droplet-combined body 30 loses fluidity, with the result that the hydrogel body 40 is obtained. A method for the gelling is not particularly limited, and for example, the gelling is performed under appropriate conditions depending on the kinds and/or concentrations of the hydrogel polymers contained in the droplet-combined body 30. Specifically, for example, when the droplet-combined body 30 contains type I collagen as each of the hydrogel polymers, the gelling may be performed by maintaining the droplet-combined body 30 at from 25° C. to 37° C. for from 15 minutes to 60 minutes.

The hydrogel body 40 includes a first hydrogel portion 41 which is a gelled body of the first hydrogel droplet 21, and a second hydrogel portion 42 which is a gelled body of the second hydrogel droplet 22 and is combined with the first hydrogel portion 41. The first hydrogel portion 41 is also a gelled body of the first droplet portion 31 of the droplet-combined body 30, and the second hydrogel portion 42 is also a gelled body of the second droplet portion 32 of the droplet-combined body 30.

As described later, in the hydrogel body 40 that has not been cultured (i.e., the hydrogel body 40 before culture or at the start of culture), the first hydrogel portion 41 contains the dispersed first cells 11 and the gelled first hydrogel polymer, and the second hydrogel portion 42 contains the dispersed second cells 12 and the gelled second hydrogel polymer.

The hydrogel body 40 does not have fluidity because it is gelled. Accordingly, also in the first hydrogel portion 41 and the second hydrogel portion 42 of the hydrogel body 40 obtained by the gelling, the first cells 11 and the second cells 12 are respectively maintained in the state of being dispersed. In the hydrogel body 40, the first hydrogel portion 41 and the second hydrogel portion 42 each have a part thereof brought into contact with the surface 111, and are combined with each other at other parts thereof.

The volume of the hydrogel body 40 that has not been cultured is not particularly limited, but may be, for example, 0.02 µL or more and 100 mL or less, 0.2 µL or more and 10 mL or less, or 2 µL or more and 1 mL or less.

The density of the cells contained in the hydrogel body 40 that has not been cultured is not particularly limited, but may be, for example, $1 \times 10^2$ cells/mL or more and $1 \times 10^9$ cells/mL or less, $1 \times 10^3$ cells/mL or more and $1 \times 10^8$ cells/mL or less, $1 \times 10^4$ cells/mL or more and $1 \times 10^8$ cells/mL or less, $1 \times 10^5$ cells/mL or more and $1 \times 10^7$ cells/mL or less, or $1 \times 10^6$ cells/mL or more and $1 \times 10^7$ cells/mL or less.

As described above, in the method of the present invention, first, a plurality of hydrogel droplets each containing dispersed cells are sequentially dropped so as to be combined with each other to form a droplet-combined body on the surface 111 of the substrate 110 in the gas phase 100, and then the droplet-combined body is gelled to provide the hydrogel body 40, which contains the dispersed cells, on the surface 111 in the gas phase 100.

Since the plurality of hydrogel droplets are combined with each other in the gas phase 100, the size of a boundary surface for an interaction between the cells in the finally formed hydrogel body 40 is simply and effectively adjusted by, for example, adjusting the size of each hydrogel droplet and/or the arrangement of the plurality of hydrogel droplets.

The first cells 11 and the second cells 12 are not particularly limited as long as the cells are living cells derived from an animal. The animal may be a human or a non-human animal (animal other than a human). The non-human animal is not particularly limited, but is preferably a non-human vertebrate (vertebrate other than a human). The non-human vertebrate is not particularly limited, but is preferably a non-human mammal. The non-human mammal is not particularly limited, but may be, for example, a primate (e.g., a monkey), a rodent (e.g., a mouse, a rat, a hamster, a guinea pig, or a rabbit), a carnivore (e.g., a dog or a cat), or an ungulate (e.g., a pig, a cow, a horse, a goat, or a sheep).

The first cells 11 and/or the second cells 12 may be differentiated cells or stem cells (undifferentiated cells). The stem cells may be totipotent stem cells, pluripotent stem cells, or tissue stem cells. Specifically, the stem cells may be, for example, induced pluripotent (iPS) stem cells, embryonic stem (ES) cells, or embryonic germ (EG) cells. The differentiated cells are not particularly limited as long as the cells have a differentiated function, but may be, for example, cells collected from a living body (which may be cells cultured after being collected from a living body) or cells induced from stem cells in vitro.

The first cells 11 and/or the second cells 12 may be cells derived from a tissue in a living body. The tissue in a living body is not particularly limited, but may be, for example, a hair follicle tissue, a skin tissue, a liver tissue, a heart tissue, a renal tissue, a nervous tissue, a bone tissue, a cartilage tissue, a bone marrow tissue, a lung tissue, a gland tissue, a periodontal tissue, or blood.

The first cells 11 and/or the second cells 12 may be adherent cells or non-adherent cells. The adherent cells are cells that are present in the state of adhering to other cells and/or an extracellular matrix in a living body. The non-adherent cells are cells that are present in a floating state in a living body (e.g., blood cells, such as lymphocytes).

The combination of the first cells 11 and the second cells 12 is not particularly limited as long as the combination is a combination of different cells that interact with each other. The combination of different cells is, for example, a combination of cells different in one or more selected from the group consisting of differentiation function, growth potential, and cell surface markers.

An interaction between the first cells 11 and the second cells 12 is not particularly limited, but for example, a combination in which a substance secreted by cells of one kind acts on cells of the other kind and/or a combination capable of forming binding between cells is preferred. When a substance secreted by cells of one kind acts on cells of the other kind, a substance secreted by the cells of the other kind may further act on the cells of the one kind. In addition, when a substance secreted by cells of one kind acts on cells of the other kind, the substance may be diffused in the hydrogel body 40 to act on the cells of the other kind, or the substance may be diffused into a solution (e.g., culture solution) containing the hydrogel body 40 and then act on the cells of the other kind in the hydrogel body 40 from within the solution.

The combination of the first cells 11 and the second cells 12 is preferably a combination of cells that interact with each other in a living body. In this case, the combination of the first cells 11 and the second cells 12 may be a combination of cells that interact with each other in the same tissue in a living body. The tissue in a living body is not particularly limited, but may be, for example, a hair follicle tissue, a skin tissue, a liver tissue, a heart tissue, a renal tissue, a nervous tissue, a bone tissue, a cartilage tissue, a bone marrow tissue, a lung tissue, a gland tissue, a periodontal tissue, or blood.

The combination of the first cells 11 and the second cells 12 may be a combination of cells derived from the same animal or a combination of cells derived from different animals. That is, the first cells 11 and the second cells 12 may both be human cells (cells derived from a human), may both be non-human animal cells (cells derived from an animal other than a human), or may be human cells and non-human animal cells, respectively, or vice versa.

The combination of the first cells 11 and the second cells 12 may be, for example, a combination of epithelial cells and mesenchymal cells. The combination of epithelial cells and mesenchymal cells is not particularly limited, but may be, for example, a combination of epithelial cells and mesenchymal cells that interact with each other in a hair follicle tissue.

In this case, the epithelial cells and/or the mesenchymal cells may be cells collected from a hair follicle tissue of a living body (which may be cells cultured after being collected from the hair follicle tissue) or cells induced from stem cells in vitro.

Specifically, the epithelial cells may be cells of the outermost layer of the outer root sheath in the bulge region of a hair follicle tissue, epithelial cells derived from the hair matrix portion, or hair follicle epithelial cells induced from stem cells (e.g., iPS cells, ES cells, or EG cells). In addition, the epithelial cells may be epithelial stem cells.

The mesenchymal cells may be hair papilla cells, dermal root sheath cells, skin mesenchymal cells in a developmental period, or hair follicle mesenchymal cells induced from stem cells (e.g., iPS cells, ES cells, or EG cells).

The first hydrogel polymer and the second hydrogel polymer are not particularly limited as long as the first hydrogel polymer and the second hydrogel polymer are each a hydrophilic polymer having a gelling ability. The first hydrogel polymer and/or the second hydrogel polymer may be a naturally occurring polymer or an artificially synthesized polymer, but is preferably a naturally occurring polymer. In addition, the first hydrogel polymer and/or the second hydrogel polymer are preferably a biocompatible polymer.

The first hydrogel polymer and/or the second hydrogel polymer are preferably an extracellular matrix. The extracellular matrix is not particularly limited as long as the extracellular matrix exists in a living body.

The first hydrogel polymer may have a cell binding property with respect to the first cells 11, and/or the second hydrogel polymer may have a cell binding property with respect to the second cells 12. A hydrogel polymer having a cell binding property is a polymer that binds to a cell surface molecule, and has, for example, a particular amino acid sequence and/or sugar chain that specifically or non-specifically binds to the cell surface molecule.

Specifically, the hydrogel polymer having a cell binding property may be, for example, one or more selected from the group consisting of collagen (e.g., one or more selected from the group consisting of type I, type II, type III, type IV, type V, and type XI), fibronectin, laminin, elastin, glycosaminoglycans (e.g., hyaluronic acid), proteoglycans, fibrin, and gelatin.

In addition, the hydrogel polymer may be one or more selected from the group consisting of gelatin, agarose, sodium alginate, and synthetic polymers (e.g., polyacrylamide, polyvinyl alcohol, methylcellulose, and polyethylene oxide).

The first hydrogel polymer and the second hydrogel polymer may be polymers of the same kind or polymers of different kinds. That is, for example, the first hydrogel polymer and the second hydrogel polymer may both be type I collagen, or may be as follows: the first hydrogel polymer is type I collagen, and the second hydrogel polymer is a glycosaminoglycan.

The substrate 110 is not particularly limited as long as the hydrogel droplets 21 and 22, the droplet-combined body 30, and the hydrogel body 40 can be formed on the surface 111 thereof. The substrate 110 may be, for example, a resin, glass, ceramics, or metal substrate.

The surface 111 of the substrate 110 is not particularly limited as long as the hydrogel droplets 21 and 22, the droplet-combined body 30, and the hydrogel body 40 can be formed thereon, but is preferably a water-repellent surface.

The water contact angle of the water-repellent surface may be, for example, 90° or more, and is preferably 100° or more, more preferably 105° or more, particularly preferably 110° or more.

The surface 111 that is water-repellent is achieved by, for example, the use of the substrate 110 that is made of a water-repellent material (e.g., a hydrophobic resin, such as a fluorine-containing polymer), and/or water-repellent treatment (e.g., modification with a hydrophobic functional group, such as a fluorine-containing functional group). In addition, the surface 111 of the substrate 110 is preferably flat.

The gas phase 100 is not particularly limited as long as the gas phase 100 is a phase of a gas, but the gas preferably contains oxygen, and air is preferably used. In the formation of the first hydrogel droplet 21, the formation of the second hydrogel droplet 22 (formation of the droplet-combined body 30), and the formation of the hydrogel body 40, the respective gas compositions of the gas phase 100 may be identical to or different from each other.

The method of the present invention may further include culturing the first cells 11 and the second cells 12 in the hydrogel body 40. In this case, the hydrogel body 40 is immersed in a culture solution, and the first cells 11 and the second cells 12 are cultured in the hydrogel body 40.

The culture solution is not particularly limited as long as the culture solution is an aqueous solution having properties, such as composition, pH, and osmotic pressure, required for maintaining the survival of the first cells 11 and the second cells 12. As components to be contained in the culture solution, there are given, for example, sugars, amino acids, vitamins, inorganic salts, antibiotics, and growth factors.

A culture time is not particularly limited, and may be, for example, 12 hours or more and 10 days or less, or 1 day or more and 7 days or less.

A culture temperature is not particularly limited as long as the culture temperature falls within a range in which the survival of the first cells 11 and the second cells 12 can be maintained. The culture temperature may be, for example, 25° C. or more and 40° C. or less, and is preferably 30° C. or more and 39° C. or less.

In the method of the present invention, the first cells 11 and the second cells 12 may be cultured in the hydrogel body 40 on the surface 111 of the substrate 110. In this case, for example, the surface 111 having the hydrogel body 40 formed thereon is immersed in a culture solution, and in the culture solution, the first cells 11 and the second cells 12 are cultured in the hydrogel body 40 fixed onto the surface 111.

In the method of the present invention, the first cells 11 and the second cells 12 may be cultured in the hydrogel body 40 after the hydrogel body 40 is removed from the surface 111. In this case, first, the hydrogel body 40 is removed from the surface 111 and recovered. A method of removing the hydrogel body 40 from the surface 111 is not particularly limited as long as the method causes the hydrogel body 40 to be removed from the surface 111 while maintaining the survival of the cells contained in the hydrogel body 40, but for example, a method involving immersing the surface 111 in an aqueous solution, such as a culture solution, or a method involving applying a flow of an aqueous solution, such as a culture solution, to the surface 111 is preferably used.

In the method of the present invention, since the hydrogel body 40 that has been removed from the surface 111 and recovered is used as it is for the culture of the cells in the hydrogel body 40, it is preferred to remove the hydrogel body 40 from the surface 111 without performing enzymatic treatment for decomposing the hydrogel polymers contained in the hydrogel body 40.

After the hydrogel body 40 is removed from the surface 111, the hydrogel body 40 may be fixed onto a surface of another substrate to culture the first cells 11 and the second cells 12 in the hydrogel body 40 on this surface.

Figure 5A:
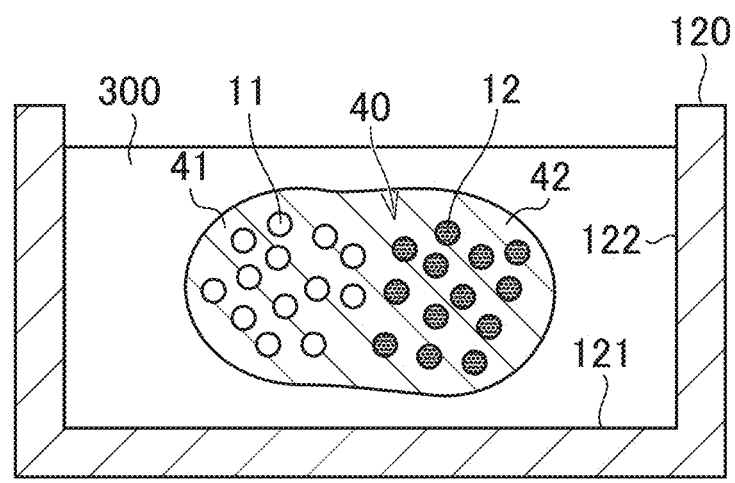
FIG. 5A is an explanatory diagram for schematically illustrating some of culture operations included in an example of the method of producing a cell-containing hydrogel body according to one embodiment of the present invention.

In the method of the present invention, after the hydrogel body 40 is removed from the surface 111, as illustrated in FIG. 5A, the first cells 11 and the second cells 12 may be cultured in the hydrogel body 40 which is in a floating state.

In this case, first, the hydrogel body 40 that has been removed from the surface 111 and recovered is immersed in a culture solution 300 in a culture vessel 120, and the first cells 11 and the second cells 12 contained in the hydrogel body 40 are cultured in a state in which the hydrogel body 40 is floating in the culture solution 300.

The state in which the hydrogel body 40 is floating in the culture solution 300 is a state in which the hydrogel body 40 is substantially free from adhering to wall surfaces 121 and 122 of the culture vessel 120. That is, for example, the hydrogel body 40 in a floating state is not only the hydrogel body 40 floating in the culture solution 300 in which there is no flow, but also the hydrogel body 40 in the state of adhering to the wall surfaces 121 and 122 of the culture vessel 120 so weakly as to be easily removed from the wall surfaces 121 and 122 when a flow is generated in the culture solution 300.

Figure 5B:
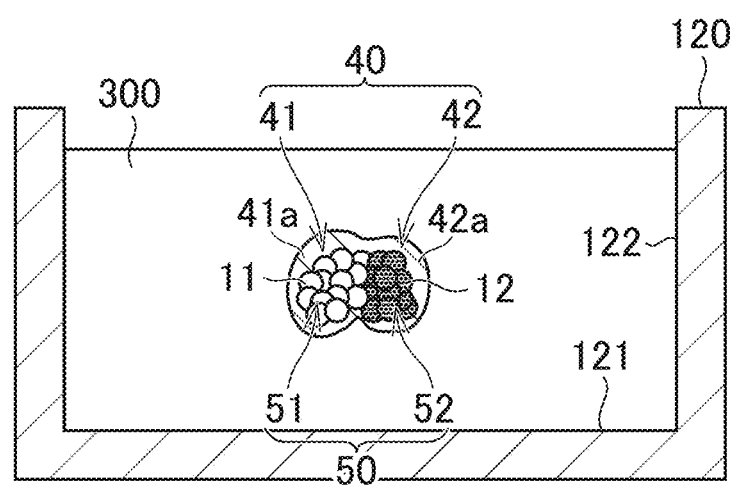
FIG. 5B is an explanatory diagram for schematically illustrating other culture operations included in an example of the method of producing a cell-containing hydrogel body according to one embodiment of the present invention.

In the method of the present invention, as illustrated in FIG. 5B, the hydrogel body 40 may be cultured to provide a hydrogel body 40 that contains a first cell aggregate 51 formed through aggregation of the first cells 11 and/or a second cell aggregate 52 formed through aggregation of the second cells 12.

The first cell aggregate 51 is formed by the first cells 11 binding to each other and spontaneously aggregating in the hydrogel body 40. Similarly, the second cell aggregate 52 is formed by the second cells 12 binding to each other and spontaneously aggregating in the hydrogel body 40.

When the first cells 11 and the second cells 12 form binding in the hydrogel body 40, as illustrated in FIG. 5B, the hydrogel body 40 that contains the first cell aggregate 51 and the second cell aggregate 52 bound to the first cell aggregate 51 is obtained.

A cell-containing hydrogel body according to one embodiment of the present invention is the hydrogel body 40 obtained as described above. The hydrogel body 40 includes: a first hydrogel portion 41, which is a gelled body of a first hydrogel droplet 21 containing first cells 11 and a first hydrogel polymer; and a second hydrogel portion 42, which is a gelled body of a second hydrogel droplet 22 containing second cells 12 and a second hydrogel polymer, and that is combined with the first hydrogel portion 41, wherein the first hydrogel portion 41 contains a first cell aggregate 51 that is an aggregated body of the first cells 11, and/or wherein the second hydrogel portion 42 contains a second cell aggregate 52 that is an aggregated body of the second cells 12.

The hydrogel body 40 that contains the first cell aggregate and/or the second cell aggregate 52 may be adhered to a surface of a substrate, but may be in a floating state in a solution. That is, the hydrogel body 40 may be floating in a solution such as the above-mentioned culture solution.

When, as described above, a plurality of hydrogel droplets are first combined with form the hydrogel body 40 in the gas phase 100, and then cells are cultured in the hydrogel body 40 to form a plurality of cell aggregates, the size of a boundary surface for an interaction between the plurality of cell aggregates in the hydrogel body 40 to be finally obtained can be simply and effectively controlled by, for example, adjusting the sizes of the plurality of hydrogel droplets and/or the arrangement of the plurality of hydrogel droplets.

In the cultured hydrogel body 40, the first cell aggregate 51 and the second cell aggregate 52 may be formed apart from each other, but as illustrated in FIG. 5B, the first cell aggregate 51 and the second cell aggregate 52 may be bound to each other.

In this case, some of the first cells 11 contained in the first cell aggregate 51 form binding with some of the second cells 12 contained in the second cell aggregate 52. As a result, as illustrated in FIG. 5B, a composite cell aggregate 50, which includes the first cell aggregate 51 and the second cell aggregate 52 bound to each other, is formed in the hydrogel body 40.

Specifically, for example, when the first cells 11 are hair follicle epithelial cells (e.g., epithelial stem cells derived from a hair follicle tissue) and the second cells 12 are hair follicle mesenchymal cells (e.g., hair papilla cells), the composite cell aggregate 50 that is a hair follicle primordium may be formed in the following manner: in the hydrogel body 40, the first cells 11 form the first cell aggregate 51 and the second cells 12 form the second cell aggregate 52, and further, the first cell aggregate 51 and the second cell aggregate 52 bind to each other.

When, as described above, a plurality of hydrogel droplets are first combined with form the hydrogel body 40 in the gas phase 100, and then cells are cultured in the hydrogel body 40 to form a plurality of cell aggregates bound to each other, the size of a binding surface between the plurality of cell aggregates in the hydrogel body 40 to be finally obtained can be simply and effectively controlled by, for example, adjusting the sizes of the plurality of hydrogel droplets and/or the arrangement of the plurality of hydrogel droplets.

The hydrogel body 40 that contains the first cell aggregate 51 and/or the second cell aggregate 52 is effectively produced by culturing the first cells 11 and the second cells 12 in the floating hydrogel body 40 after removing the hydrogel body 40 from the surface 111.

In the method of the present invention, the hydrogel body 40 (FIG. 5A) that contains the dispersed first cells 11 and the dispersed second cells 12 may be cultured to provide a shrunken hydrogel body 40 (FIG. 5B) that contains the first cell aggregate 51 and/or the second cell aggregate 52.

That is, when the cells 11 and 12 are bound to each other and gradually aggregate to form the cell aggregates 51 and 52 in the hydrogel body 40, the hydrogel body 40 shrinks with the progress of culture time.

Specifically, the ratio of the volume of the hydrogel body 40 that contains the first cell aggregate 51 and/or the second cell aggregate 52 to the volume of the hydrogel body 40 at the start of culture, which contains the first cells 11 and the second cells 12 that are dispersed, may be, for example, 50% or less, 40% or less, 30% or less, 20% or less, or 10% or less.

Such shrinkage of the hydrogel body 40 with the progress of culture becomes remarkable when the first hydrogel polymer has a cell binding property with respect to the first cells 11, and/or the second hydrogel polymer has a cell binding property with respect to the second cells 12.

The density of cells in the hydrogel body 40 containing the first cell aggregate 51 and/or the second cell aggregate 52 (number of cells contained in a unit volume of the hydrogel body 40) may be, for example, $1 \times 10^2$ cells/mL or more and $1 \times 10^{11}$ cells/mL or less, $1 \times 10^3$ cells/mL or more and $1 \times 10^{10}$ cells/mL or less, $1 \times 10^4$ cells/mL or more and $1 \times 10^{10}$ cells/mL or less, $1 \times 10^5$ cells/mL or more and $1 \times 10^9$ cells/mL or less, or $1 \times 10^6$ cells/mL or more and $1 \times 10^9$ cells/mL or less.

In the method of the present invention, as illustrated in FIG. 5B, the first cells 11 and the second cells 12 may be cultured in the hydrogel body 40 to provide a hydrogel body 40 having the following property (a) and/or property (b): (a) the hydrogel body contains the first cell aggregate 51 and a first hydrogel covering portion 41a covering the first cell aggregate 51, and a density of the first hydrogel polymer inside the first cell aggregate 51 is higher than that in the first hydrogel covering portion 41a; (b) the hydrogel body contains the second cell aggregate 52 and a second hydrogel covering portion 42a covering the second cell aggregate 52, and a density of the second hydrogel polymer inside the second cell aggregate 52 is higher than that in the second hydrogel covering portion 42a.

That is, as illustrated in FIG. 5A and FIG. 5B, when the first cells 11 aggregate to form the first cell aggregate 51 and/or the second cells 12 aggregate to form the second cell aggregate 52 in the hydrogel body 40 with the progress of culture time, a hydrogel part between the first cells 11 and/or between the second cells 12 shrinks remarkably compared to a hydrogel part covering the first cell aggregate 51 and/or the second cell aggregate 52.

As a result, in the hydrogel body 40 containing the first cell aggregate 51 and/or the second cell aggregate 52, the density of the first hydrogel polymer inside the first cell aggregate 51 becomes higher than that in the first hydrogel covering portion 41a, and/or the density of the second hydrogel polymer inside the second cell aggregate 52 becomes higher than that in the second hydrogel covering portion 42a.

Such local concentrating of the first hydrogel polymer and/or the second hydrogel polymer becomes remarkable particularly when the first hydrogel polymer has a cell binding property with respect to the first cells 11, and/or the second hydrogel polymer has a cell binding property with respect to the second cells 12.

That is, in this case, since the first cells 11 and/or the second cells 12 aggregate while pulling the hydrogel polymer to which cells are adhering toward themselves, a hydrogel polymer in the vicinity of the first cells 11 and/or the second cells 12 is remarkably concentrated compared to a hydrogel polymer distant from the first cells 11 and/or the second cells 12.

The distribution of the density of a hydrogel polymer in the hydrogel body 40 may be identified by, for example, using a staining method specific to the hydrogel polymer. Specifically, for example, the density of the first hydrogel polymer in the first cell aggregate 51 and the density of the first hydrogel polymer in the first hydrogel covering portion 41a may be quantitatively compared by: staining the first hydrogel polymer contained in the hydrogel body 40 with a fluorescence-labeled antibody; observing the hydrogel body 40 after the staining under a fluorescence microscope; and comparing a fluorescence intensity in the first cell aggregate 51 and a fluorescence intensity in the first hydrogel covering portion 41a.

Specifically, in the hydrogel body 40 that contains the first cell aggregate 51, the density of the first hydrogel polymer inside the first cell aggregate 51 may be, for example, 2 or more times, 5 or more times, or 10 or more times the density of the first hydrogel polymer in the first hydrogel covering portion 41a.

Such uneven distribution of a hydrogel polymer in the hydrogel body 40 results from the characteristic operations of the method of the present invention of first forming the hydrogel body 40 containing dispersed cells in the gas phase 100 and then culturing the cells in the hydrogel body 40 to form cell aggregates.

In the hydrogel body 40 to be produced by the method of the present invention, the size of a boundary surface for an interaction between the first cells 11 and the second cells 12, and/or the size of a boundary surface for an interaction between the first cell aggregate 51 and the second cell aggregate 52 (their binding surface when the first cell aggregate 51 and the second cell aggregate 52 are bound to each other) can be arbitrarily set, and hence the hydrogel body 40 is useful as, for example, a research tool for an interaction between cells, or a tissue body for transplantation in which a desired interaction between cells is achieved.

Specifically, for example, the hydrogel body 40 that contains a hair follicle primordium formed through binding of a cell aggregated body of hair follicle epithelial cells and a cell aggregated body of hair follicle mesenchymal cells as described above also enables the number of hairs grown from the hair follicle primordium after transplantation to be adjusted by adjusting the size of the binding surface of the two cell aggregated bodies.

Accordingly, the present invention is useful, for example, for the treatment of a patient having damaged hair follicles due to a disease, an accident, or the like, or as a research tool for the treatment. Examples of the disease to which the present invention is applicable include androgenetic alopecia (AGA), female androgenetic alopecia (FAGA), postpartum alopecia, diffuse alopecia, seborrheic alopecia, alopecia pityroides, traction alopecia, alopecia caused by metabolic disorders, pressure alopecia, alopecia areata, neurotic alopecia, hair-pulling disorder, alopecia universalis, and symptomatic alopecia.

In addition, the hydrogel body 40 to be produced by the method of the present invention is not limited to a hair follicle tissue, and is also useful, for example, as a tissue body reconstructing in vitro a tissue such as a hair follicle tissue, a skin tissue, a liver tissue, a heart tissue, a renal tissue, a nervous tissue, a bone tissue, a cartilage tissue, a bone marrow tissue, a lung tissue, a gland tissue, a periodontal tissue, or blood, for the treatment of a disease (e.g., utilization as a transplantation tissue), or as a research tool for, for example, searching for a substance that may be used for the treatment or prevention of a disease associated with hair loss and/or searching for a substance involved in the mechanism of the disease.

Next, specific Examples according to the embodiments of the present invention will be described.

Example 1

[Collection of Epithelial Cells and Mesenchymal Cells]
A dorsal skin tissue was collected from a C57BL/6 mouse embryo at embryonic day 18, and was subjected to dispase treatment using a partially modified version of a method reported by Nakao et al. (Koh-ei Toyoshima et al. Nature Communications, 3, 784, 2012) at 4° C. under the shaking condition of 30 rpm for 1 hour to separate the epithelial layer and mesenchymal layer of the skin tissue. After that, the epithelial layer was treated with 100 U/mL collagenase for 1 hour and 20 minutes and further treated with trypsin for 10 minutes to isolate epithelial cells. In addition, the mesenchymal layer was treated with 100 U/mL collagenase for 1 hour and 20 minutes to isolate mesenchymal cells.

[Formation of Cell-Containing Hydrogel Bodies]
The mesenchymal cells collected as described above were suspended in a type I collagen solution (collagen Type 1-A, manufactured by Nitta Gelatin Inc.) to prepare a first hydrogel cell suspension containing the dispersed mesenchymal cells at a density of $1 \times 10^4$ cells/2 μL. Subsequently, in the atmosphere, about 2 μL of the first hydrogel cell suspension was dropped onto a water-repellent surface of a polystyrene substrate to form a first hydrogel droplet containing dispersed mesenchymal cells.

Meanwhile, the epithelial cells collected as described above were suspended in a type I collagen solution (collagen Type 1-A, manufactured by Nitta Gelatin Inc.) to prepare a second hydrogel cell suspension containing the dispersed epithelial cells at a density of $1 \times 10^4$ cells/2 μL. Subsequently, in the atmosphere, about 2 μL of the second hydrogel cell suspension was dropped to a position on the water-repellent surface adjacent to the first hydrogel droplet to form a second hydrogel droplet containing dispersed epithelial cells and being combined with the first hydrogel droplet. Thus, hydrogel droplet-combined bodies each formed by combining the first hydrogel droplet and the second hydrogel droplet were obtained on the water-repellent surface in the atmosphere.

After that, in the atmosphere, the cell-containing hydrogel bodies were obtained by incubating the hydrogel droplet-combined bodies on the water-repellent surface at 37° C. for 30 minutes for gelling the collagen.

[Culture of Cell-Containing Hydrogel Bodies]
A culture solution was poured on the cell-containing hydrogel bodies, which had been formed as described above, with a pipette, and thus the cell-containing hydrogel bodies were removed from the water-repellent surface and recovered, and were dispersed in the culture solution. A mixed medium of DMEM medium and KG2 medium (containing 10% fetal bovine serum and 1% penicillin) was used as the culture solution.

Subsequently, with use of a 96-well plate for suspension culture (Primesurface (trademark) 96U plate) as a culture vessel, 100 μL aliquots of the culture solution containing the cell-containing hydrogel bodies were added so that each well of the plate contained one of the cell-containing hydrogel bodies. After that, the cell-containing hydrogel bodies were cultured in a floating state in the wells for 3 days.

Figure 6A:
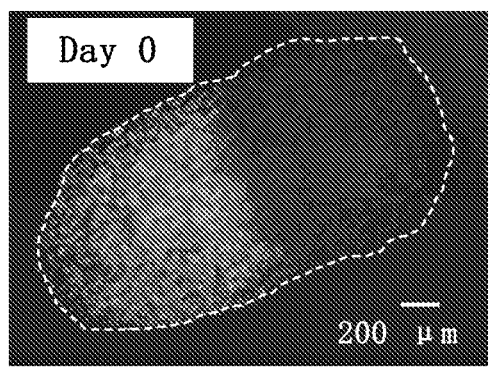
FIG. 6A is an explanatory diagram showing a fluorescence micrograph of a cell-containing hydrogel body on the initial day of culture in Example 1 according to one embodiment of the present invention.
Figure 6B:
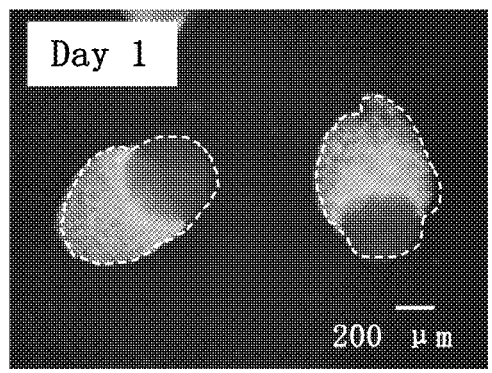
FIG. 6B is an explanatory diagram showing a fluorescence micrograph of cell-containing hydrogel bodies on day 1 of culture in Example 1 according to one embodiment of the present invention.
Figure 6C:
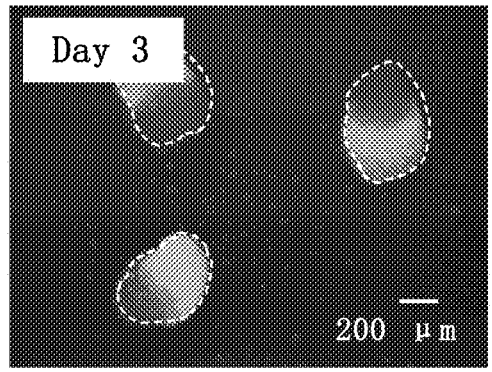
FIG. 6C is an explanatory diagram showing a fluorescence micrograph of cell-containing hydrogel bodies on day 3 of culture in Example 1 according to one embodiment of the present invention.

[Results]
In FIG. 6A, FIG. 6B, and FIG. 6C, fluorescence micrographs of cell-containing hydrogel bodies on the initial day (D0) of culture, day 1 (D1) of culture, and day 3 (D3) of culture are shown, respectively. Parts shown in a whitish color in FIG. 6A to FIG. 6C are mesenchymal cells having their cell membranes stained in advance with a fluorescent dye (Vybrant (trademark) DiI Cell-Labeling Solution). In addition, parts surrounded by white dashed lines in FIG. 6A to FIG. 6C are cell-containing hydrogel bodies. The scale bar in each of FIG. 6A to FIG. 6C represents 200 μm.

Figure 7:
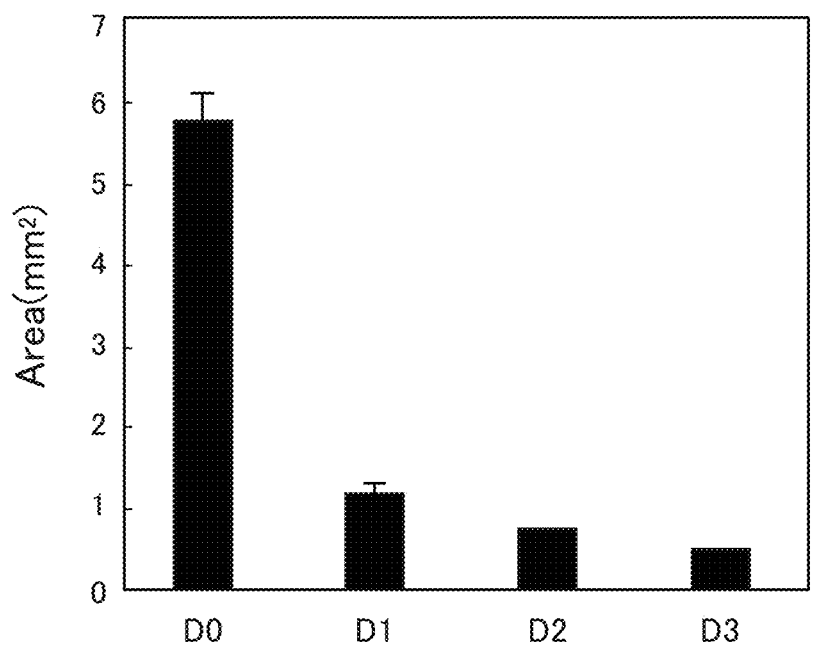
FIG. 7 is an explanatory diagram showing the results of evaluation of the projected areas of cell-containing hydrogel bodies under a phase-contrast microscope in Example 1 according to one embodiment of the present invention.

In FIG. 7, the results of evaluation of the projected areas (mm²) of the cell-containing hydrogel bodies on the initial day (D0) of culture, day 1 (D1) of culture, day 2 (D2) of culture, and day 3 (D3) of culture under a phase-contrast microscope are shown (n=10).

As shown in FIG. 6A to FIG. 6C and FIG. 7, as the culture time progressed, in each of the cell-containing hydrogel bodies, the mesenchymal cells spontaneously aggregated with each other and the epithelial cells spontaneously aggregated with each other to respectively form a mesenchymal cell aggregate and an epithelial cell aggregate, and besides, the cell-containing hydrogel body shrank. In addition, in each of the cell-containing hydrogel bodies, the mesenchymal cell aggregate and the epithelial cell aggregate had formed binding.

Calculation based on the results of FIG. 7 found that the volume of the cell-containing hydrogel bodies on day 1 of culture was about 5% of that of the cell-containing hydrogel bodies on the initial day of culture, and the volume of the cell-containing hydrogel bodies on day 3 of culture was about 1% of the volume of the cell-containing hydrogel bodies on the initial day of culture.

Such shrinkage of the cell-containing hydrogel bodies with the progress of culture was presumed to have occurred because, for example, the cells contained in the cell-containing hydrogel bodies adhered to fibers of collagen gel, and further, the cells aggregated while pulling the collagen gel toward themselves.

Example 2

[Collection of Epithelial Cells and Mesenchymal Cells]
Epithelial cells and mesenchymal cells were each isolated from a skin tissue of a C57BL/6 mouse embryo at embryonic day 18 in the same manner as in Example 1 described above.
[Formation of Cell-Containing Hydrogel Bodies]
In the same manner as in Example 1 described above, in the atmosphere, on a water-repellent surface, first hydrogel droplets each containing dispersed mesenchymal cells and second hydrogel droplets each containing dispersed epithelial cells were combined with form hydrogel droplet-combined bodies, and further, the hydrogel droplet-combined bodies were gelled to form cell-containing hydrogel bodies.
[Culture of Cell-Containing Hydrogel Bodies]
In the same manner as in Example 1 described above, the cell-containing hydrogel bodies were removed from the water-repellent surface and recovered, and were cultured in a floating state in a mixed medium for 3 days.
[Transplantation to Mouse]
The cell-containing hydrogel bodies cultured for 3 days as described above (hair follicle primordia produced in vitro) were recovered and intradermally transplanted to a nude mouse. That is, the nude mouse was anesthetized by inhalation of isoflurane, and the dorsal part thereof was disinfected with Isodine. Subsequently, a V-lance micro-scalpel (Alcon Japan Ltd.) was used to form incisions for transplantation ranging from the epidermal layer of the skin to a lower part of the dermal layer. Then, the incisions for transplantation were each injected with one of the cell-containing hydrogel bodies. The care of the nude mouse and the transplantation experiment were performed in conformity with the guidelines of the animal experimental committee at Yokohama National University.
[Results]
In FIG. 8A, FIG. 8B, and FIG. 8C, photographs of hairs grown from the cell-containing hydrogel bodies transplanted to the nude mouse on day 11 after transplantation, day 19 after transplantation, and day 24 after transplantation are shown, respectively.

Figure 8A:
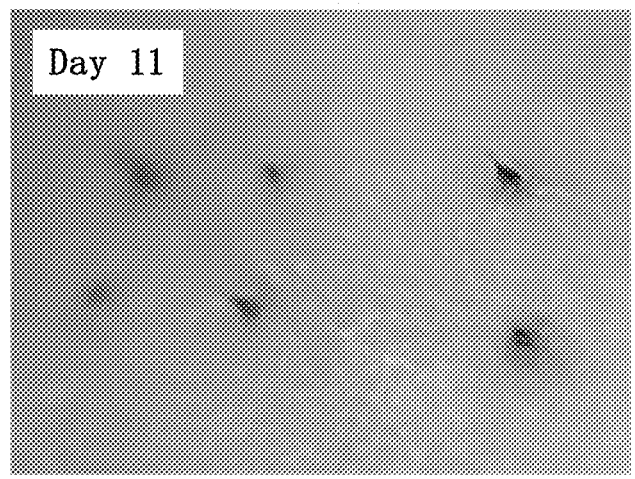
FIG. 8A is an explanatory diagram showing a photograph of cell-containing hydrogel bodies, from which hair has grown, on day 11 after transplantation in Example 2 according to one embodiment of the present invention.
Figure 8B:
FIG. 8B is an explanatory diagram showing a photograph of cell-containing hydrogel bodies, from which hair has grown, on day 19 after transplantation in Example 2 according to one embodiment of the present invention.
Figure 8C:
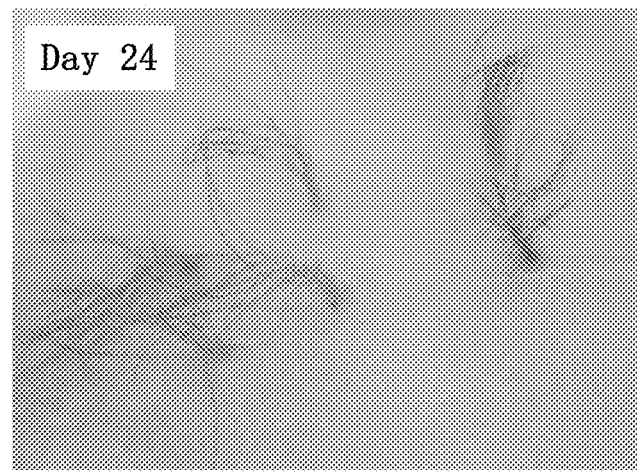
FIG. 8C is an explanatory diagram showing a photograph of cell-containing hydrogel bodies, from which hair has grown, on day 24 after transplantation in Example 2 according to one embodiment of the present invention.

As shown in FIG. 8A to FIG. 8C, hair growth from the transplanted cell-containing hydrogel bodies was recognized on day 11 after transplantation. Then it was recognized on day 19 after transplantation and day 24 after transplantation that hair was further lengthened. That is, the cell-containing hydrogel bodies produced as described above were shown to be useful for treatment or research concerning hair regeneration.

Example 3

[Collection of Epithelial Cells and Mesenchymal Cells]
Epithelial cells and mesenchymal cells were each isolated from a skin tissue of a C57BL/6 mouse embryo at embryonic day 18 in the same manner as in Example 1 described above.
[Formation of Cell-Containing Hydrogel Bodies]
In the same manner as in Example 1 described above, in the atmosphere, on a water-repellent surface, first hydrogel droplets each containing dispersed mesenchymal cells and second hydrogel droplets each containing dispersed epithelial cells were combined with form hydrogel droplet-combined bodies, and further, the hydrogel droplet-combined bodies were gelled to form cell-containing hydrogel bodies.
[Culture of Cell-Containing Hydrogel Body]
The cell-containing hydrogel bodies were subjected to suspension culture in a mixed medium for 3 days in the same manner as in Example 1 described above.
[Formation of Spheroid-Fused Tissue]
Meanwhile, as a comparative control, a spheroid-fused tissue was produced by fusing an epithelial cell spheroid and a mesenchymal cell spheroid to each other, each of which having been formed in advance. That is, first, epithelial cells and mesenchymal cells were each isolated from a skin tissue of a C57BL/6 mouse embryo at embryonic day 18 in the same manner as in Example 1 described above.

Subsequently, a cell suspension containing dispersed epithelial cells was inoculated into each well of a 96-well spheroid culture plate (Prime surface 96U, manufactured by Sumitomo Bakelite Co., Ltd.) at $1 \times 10^4$ cells/100 µL.

Then, the epithelial cells were subjected to suspension culture in each well for 1 day to allow the epithelial cells to spontaneously aggregate, to thereby form one epithelial cell spheroid as an aggregate of the epithelial cells in each well.

Similarly, the mesenchymal cells were subjected to suspension culture in each well for 1 day to allow the mesenchymal cells to spontaneously aggregate, to thereby form one mesenchymal cell spheroid as an aggregate of the mesenchymal cells in each well.

Further, one epithelial cell spheroid and one mesenchymal cell spheroid were placed in the same well, and subjected to suspension culture for 6 days. A mixed medium of DMEM medium and KG2 medium (containing 10% fetal bovine serum and 1% penicillin) was used as a culture solution. In the culture of the spheroid mixture, one epithelial cell spheroid and one mesenchymal cell spheroid fused to each other with the progress of culture time to form one spheroid-fused tissue.
[Results]
In FIG. 9A, FIG. 9B, and FIG. 9C, fluorescence micrographs of the spheroid-fused tissue on day 1, day 3, and day 6 of culture are shown, respectively. In FIG. 10A, FIG. 10B, and FIG. 10C, fluorescence micrographs of the cell-containing hydrogel body on day 1, day 3, and day 6 of culture are shown, respectively. In each of the figures, the part surrounded by a white dashed line is the spheroid-fused tissue or the cell-containing hydrogel body. In addition, the part shown in a whitish color in the spheroid-fused tissue or the cell-containing hydrogel body of each figure indicates mesenchymal cells having their cell membranes stained in advance with a fluorescent dye (Vybrant (trademark) DiI Cell-Labeling Solution). The scale bar in each figure represents 200 μm.

Figure 9A:
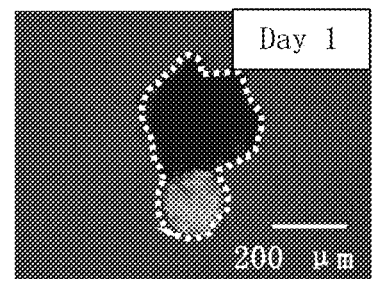
FIG. 9A is an explanatory diagram showing a fluorescence micrograph of a spheroid-fused tissue on day 1 of culture in Example 3 according to one embodiment of the present invention.
Figure 9B:
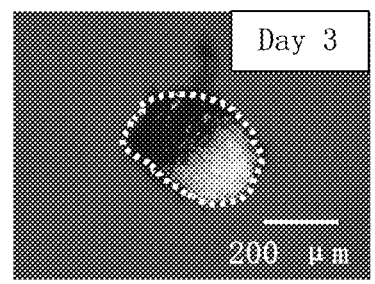
FIG. 9B is an explanatory diagram showing a fluorescence micrograph of a spheroid-fused tissue on day 3 of culture in Example 3 according to one embodiment of the present invention.
Figure 9C:
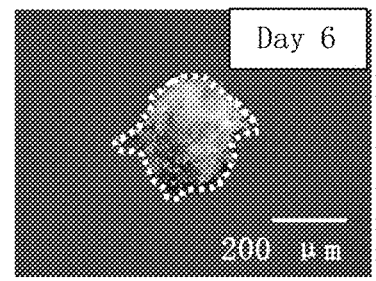
FIG. 9C is an explanatory diagram showing a fluorescence micrograph of a spheroid-fused tissue on day 6 of culture in Example 3 according to one embodiment of the present invention.
Figure 10A:
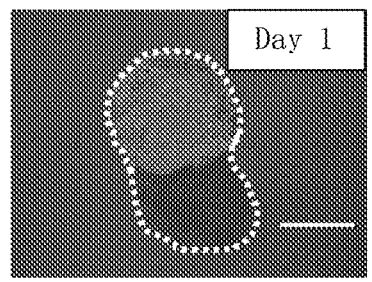
FIG. 10A is an explanatory diagram showing a fluorescence micrograph of a cell-containing hydrogel body on day 1 of culture in Example 3 according to one embodiment of the present invention.
Figure 10B:
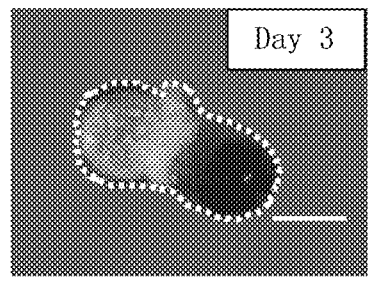
FIG. 10B is an explanatory diagram showing a fluorescence micrograph of a cell-containing hydrogel body on day 3 of culture in Example 3 according to one embodiment of the present invention.
Figure 10C:
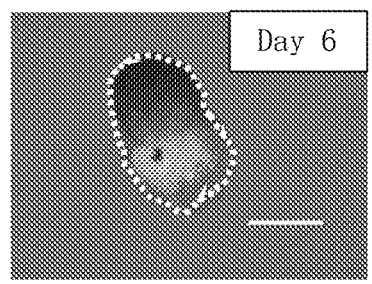
FIG. 10C is an explanatory diagram showing a fluorescence micrograph of a cell-containing hydrogel body on day 6 of culture in Example 3 according to one embodiment of the present invention.

As shown in FIG. 9A to FIG. 9C, with the progress of culture time, the shape of the spheroid-fused tissue changed significantly and the cells therein migrated, and on day 6 of culture, the epithelial cells and the mesenchymal cells were present as a mixture throughout the entire tissue.

On the other hand, as shown in FIG. 10A to FIG. 10C, in the cell-containing hydrogel body, on day 1 of culture, the epithelial cells had aggregated to form an epithelial cell aggregate, and the mesenchymal cells had aggregated to form a mesenchymal cell aggregated body. Then, after day 1 of culture, the shape of the cell-containing hydrogel body hardly changed, and a portion containing the epithelial cell aggregated body and a portion containing the mesenchymal cell aggregated body were stably maintained.

That is, in the cell-containing hydrogel body, a boundary between the epithelial cell aggregated body and the mesenchymal cell aggregated body was stably maintained throughout the culture period. Black spots observed on the mesenchymal cell aggregate in the cell-containing hydrogel body shown in FIG. 10C were presumed to indicate the presence of a melanin pigment.

The invention claimed is:

1. A method of producing a cell-containing hydrogel body, comprising:
    forming, under a gas phase, a first hydrogel droplet on a surface of a substrate, the first hydrogel droplet containing first cells being dispersed therein and a first hydrogel polymer;
    forming, under a gas phase, a second hydrogel droplet on the surface, the second hydrogel droplet containing second cells being dispersed therein and a second hydrogel polymer, the second hydrogel droplet being positioned adjacent to and in contact with the first hydrogel droplet;
    forming, under a gas phase, a cell-containing hydrogel body on the surface by gelling a hydrogel droplet-combined body including a first droplet portion derived from the first hydrogel droplet and a second droplet portion derived from the second hydrogel droplet, and
    culturing the first cells and the second cells in the cell-containing hydrogel body in a floating state after the cell-containing hydrogel body is removed from the surface to obtain the cell-containing hydrogel body that contains a first cell aggregate of the first cells and a second cell aggregate of the second cells bound to the first cell aggregate,
    wherein a combination of the first cells and the second cells is a combination of epithelial cells and mesenchymal cells, and
    wherein the mesenchymal cells comprise hair follicle mesenchymal cells.

2. The method of producing a cell-containing hydrogel body according to claim 1, wherein the first cells and the second cells in the cell-containing hydrogel body are cultured to provide the cell-containing hydrogel body having the following property (a) and/or property (b):
    (a) the cell-containing hydrogel body contains the first cell aggregate and a first hydrogel covering portion covering the first cell aggregate, and a density of the first hydrogel polymer inside the first cell aggregate is higher than that in the first hydrogel covering portion;
    (b) the cell-containing hydrogel body contains the second cell aggregate and a second hydrogel covering portion covering the second cell aggregate, and a density of the second hydrogel polymer inside the second cell aggregate is higher than that in the second hydrogel covering portion.

3. The method of producing a cell-containing hydrogel body according to claim 1,
    wherein the first hydrogel polymer has a cell binding property with respect to the first cells, and/or
    wherein the second hydrogel polymer has a cell binding property with respect to the second cells.

4. The method of claim 1, wherein the first hydrogel droplet and/or the second hydrogel droplet has a volume of 0.01 μL or more and 1 mL or less.

5. The method of claim 1, the first cells contained in the first hydrogel droplet and/or the second cells contained in the second hydrogel droplet has a density of $1 \times 10^2$ cells/ml or more and $1 \times 10^9$ cells/ml or less.

6. The method of claim 1, wherein the first cells and the second cells dispersed in the cell-containing hydrogel body are cultured after the cell-containing hydrogel body is removed from the surface to obtain a shrunken hydrogel body that contains a first cell aggregate and/or a second cell aggregate.

7. The method of claim 6, wherein the shrunken hydrogel body is formed through a process that the cell-containing hydrogel body shrinks with the progress of culture time while the dispersed first cells and/or the dispersed second cells gradually aggregate to form the first cell aggregate and/or the second cell aggregate.

8. The method of claim 6, wherein a ratio of the volume of the shrunken hydrogel body that contains the first cell aggregate and/or the second cell aggregate to the volume of the hydrogel body at the start of the culture is 50% or less.

9. The method of claim 2, wherein (a) the density of the first hydrogel polymer inside the first cell aggregate is 2 or more times the density of the first hydrogel polymer in the first hydrogel covering portion; and/or (b) the density of the second hydrogel polymer inside the second cell aggregate is 2 or more times the density of the second hydrogel polymer in the second hydrogel covering portion.

10. The method of claim 1, wherein the epithelial cells comprise hair follicle epithelial cells.

11. The method of claim 10, wherein the hair follicle epithelial cells contain at least one selected from the group consisting of cells of the outermost layer of the outer root sheath in the bulge region of a hair follicle tissue, epithelial cells derived from the hair matrix portion, and hair follicle epithelial cells induced from stem cells.

12. The method of claim 10, wherein the hair follicle epithelial cells contain epithelial stem cells derived from a hair follicle tissue.

13. The method of claim 1, wherein the hair follicle mesenchymal cells contain at least one selected from the group consisting of hair papilla cells, dermal root sheath cells, and hair follicle mesenchymal cells induced from stem cells.

14. The method of claim 1, wherein the first hydrogel polymer and/or the second hydrogel polymer comprises a naturally occurring polymer or an artificially synthesized polymer.

15. The method of claim 1, wherein the first hydrogel polymer and/or the second hydrogel polymer comprises an extracellular matrix.

16. The method of claim 1, wherein the first hydrogel polymer and the second hydrogel polymer comprise the same polymer.

17. The method of claim 1, wherein the first hydrogel droplet and/or the second hydrogel droplet is formed on the surface of the substrate using an automatic dispensing system.

18. The method of claim 1, wherein the density of cells in the hydrogel body containing the first cell aggregate and/or the second cell aggregate is $1\times10^2$ cells/mL or more and $1\times10^{11}$ cells/mL or less.

19. The method of claim 1, wherein the first hydrogel polymer and the second hydrogel polymer comprise a different polymer.

* * * * *